United States Patent [19]

Kirmann

[11] Patent Number: Plant 6,014

[45] Date of Patent: Sep. 15, 1987

[54] GERANIUM PLANT NAMED BETTY

[75] Inventor: Wolfgang Kirmann, Langenzersdorf, Austria

[73] Assignee: Mirko Vavra, Bisamberg, Austria

[21] Appl. No.: 810,671

[22] Filed: Dec. 19, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Betty having white flower color, variegated with deep purple; medium green foliage; compact, self-branching growth habit; early flowering; good bud production at night temperatures up to 16° C., thus providing a long and continuous flowering period; and ease of propagation.

2 Drawing Figures

The present invention comprises a new and distinct cultivar of geranium, botanically known as *Pelargonium domesticum,* and hereinafter referred to by the cultivar name Betty.

Betty is a product of a planned breeding program which had the objective of creating new geranium cultivars having good flower production, very compact growth habit, very early flowering, long flowering period and white flower color.

Betty was originated from a hybridization made by applicant in a controlled breeding program in Bisamberg, Austria in 1982. The female parent was a cultivar designated as seedling 41/76, characterized by its very vigorous growth habit and white flower color with red markings. The male parent of Betty was Bambino, characterized by a very compact growth habit, relatively small foliage and early flowering.

Betty was discovered and selected as one flowering plant within the progeny of the stated cross by applicant on Mar. 29, 1983 in a controlled environment in Bisamberg, Austria.

The first act of asexual reproduction of Betty was accomplished when vegetative cuttings were taken from the initial selection on Aug. 25, 1983 in a controlled environment in Bisamberg, Austria by a technician working under formulations established and supervised by Wolfgang Kirmann. Horticultural examination of selected units initiated in the spring of 1984 has demonstrated that the combination of characteristics as herein disclosed for Betty are firmly fixed and are retained through successive generations of asexual reproduction.

Betty has not been observed under all possible environmental conditions. The phenotype may vary significantly with variations in environment such as temperature, light intensity, and day length. The following observations, measurements and comparisons describe plants grown in Bisamberg, Austria under conditions which approximate those generally used in commercial practice.

The following traits have been repeatedly observed and are determined to be basic characteristics of Betty, which in combination distinguish this geranium as a new and distinct cultivar.

1. White flower color, variegated with deep purple.
2. Early flowering and long flowering period.
3. Propagates well.
4. Medium green foliage.

5. Compact, self-branching growth habit, resulting in the setting of many buds.
6. Buds are produced under normal greenhouse conditions (5000 Lux for 16 hours per day) at 14°-16° C. This is well above the cooler temperatures required for previous Domesticum varieties. In addition, plants flowered indoors can be transplanted outdoors and will continue blooming at night temperatures as high as 16° C. Known Domesticum cultivars will produce buds outdoors only at night temperatures of 10° C. or lower.
7. Betty is unique with regard to the combined features of compactness, continuous flowering, floriferous habit, and white flower color.

Of the many commercial cultivars known to the present inventor, the most similar in comparison to Betty is White Swan, an unpatented but commercial cultivar. In comparison to White Swan, Betty has a more compact, stable growth habit, deeper green foliage, better bud production, more continuous flowering, and red markings in the white petals.

The accompanying photographic drawings show typical flower and foliage characteristics of Betty, with colors being as true as possible with illustrations of this type.

Sheet 1 is a perspective view of a plotted plant of Betty.

Sheet 2 is a black and white print showing the upper surface of immature and mature plants of Betty.

In the following description color references are made to The Royal Horticultural Society Colour Chart (RHS). The color values were determined at 9:00 a.m. on May 23, 1985 under 35,000 Lux light intensity in a greenhouse at Hillscheid, Federal Republic of Germany.

CLASSIFICATION

Botanical: *Pelargonium domesticum.*

Commercial: Commonly referred to as a "Martha Washington" geranium, and having the cultivar name Betty.

INFLORESCENCE

A. Umbel:

*Average diameter.*—Relatively large, 120-125 mm.

*Peduncle length.*—Normal.

*Pedicel length.*—Normal.

B. Corolla:

*Average diameter.*—80–95 mm; total inflorescence diameter is within the foliage.

*Form.*—5+petals.

*Color (general tonality from a distance of three meters).*—White, variegated with deep violet.

*Color (upper surface).*—White, variegated with 60A-B.

C. Bud:

*Shape.*—Round.

*Color.*—White.

D. Reproductive organs:

*Androecium.*—Light yellow.

*Gynoecium.*—Normal.

E. Spring flowering response period: Early.

G. Durability: Good.

PLANT

A. Foliage:

*Form.*—Zygomorphic with a nectar spur.

*Margin.*—Sharply crenate; indented.

*Color (upper surface).*—Medium green.

*Tolerance of Botrytis and soil fungi.*—Excellent except in conditions of very high humidity when botrytis may result.

B. General appearance and form:

*Internode length.*—Very short.

*Branching pattern.*—Excellent.

*Height.*—Very compact.

I claim:

1. A new and distinct cultivar of geranium named Betty, as described and illustrated, and particularly characterized by its white flower color, variegated with deep purple; medium green foliage; compact, self-branching growth habit; early flowering; good bud production at night temperatures up to 16° C., thus providing a long and continuous flowering period; and ease of propagation.

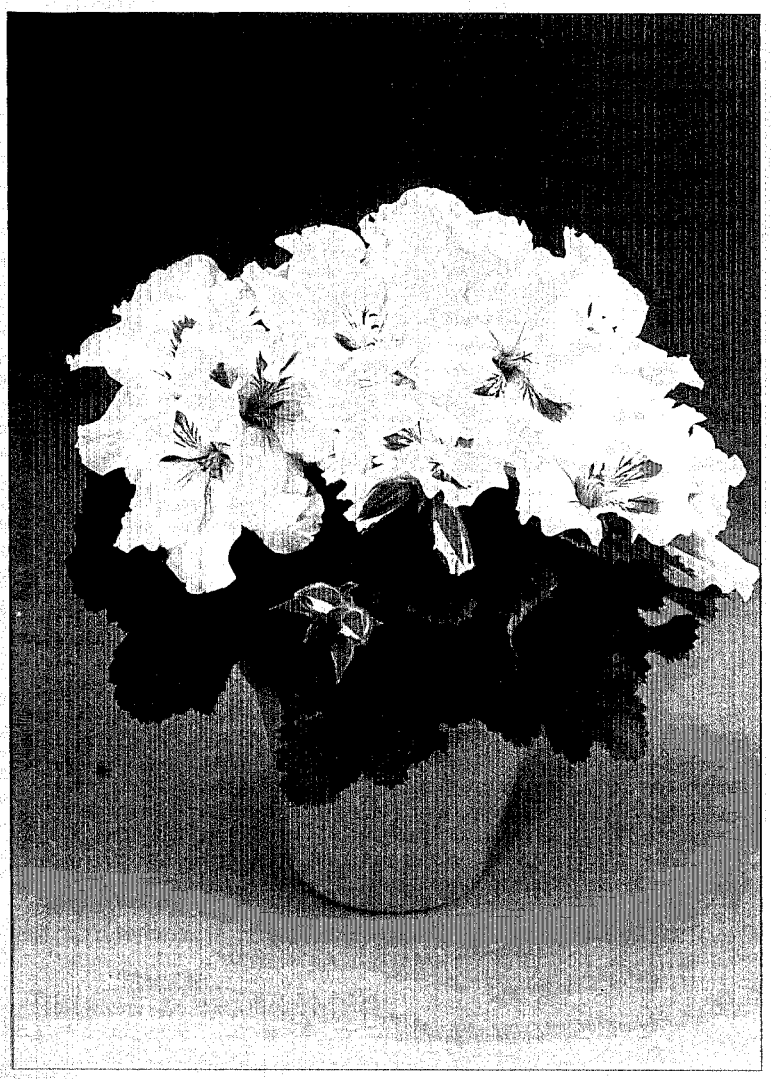

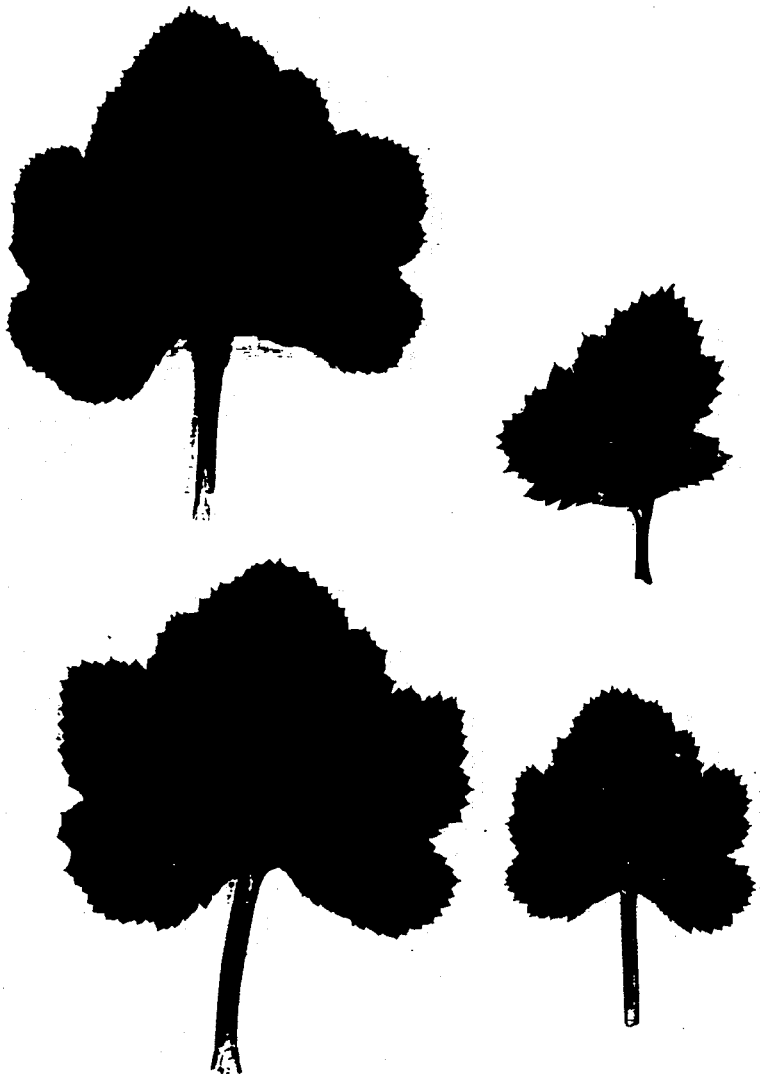

* * * * *